(12) United States Patent
Sohi et al.

(10) Patent No.: US 11,471,543 B2
(45) Date of Patent: Oct. 18, 2022

(54) PHARMACEUTICAL COMPOSITIONS OF SULFUR COLLOID AND PROCESSES THEREOF

(71) Applicant: Jubilant Generics Limited, Noida (IN)

(72) Inventors: Harmik Sohi, Noida (IN); Rahul Hasija, Noida (IN); Basant Malik, Noida (IN); Kamal S. Mehta, Noida (IN); Dinesh Kumar, Noida (IN)

(73) Assignee: Jubilant Generics Limited

( * ) Notice: Subject to any disclaimer, the term of this patent is extended or adjusted under 35 U.S.C. 154(b) by 0 days.

(21) Appl. No.: 16/630,786

(22) PCT Filed: Oct. 7, 2019

(86) PCT No.: PCT/IB2019/058517
§ 371 (c)(1),
(2) Date: Jan. 13, 2020

(87) PCT Pub. No.: WO2020/070731
PCT Pub. Date: Apr. 9, 2020

(65) Prior Publication Data
US 2021/0361785 A1    Nov. 25, 2021

(30) Foreign Application Priority Data
Oct. 6, 2018    (IN) .............................. 201811038067

(51) Int. Cl.
| | | |
|---|---|---|
| *A61K 51/12* | (2006.01) |
| *A61K 9/19* | (2006.01) |
| *A61K 47/18* | (2017.01) |
| *A61K 47/20* | (2006.01) |
| *A61K 47/38* | (2006.01) |
| *A61K 47/42* | (2017.01) |
| *A61K 51/02* | (2006.01) |

(52) U.S. Cl.
CPC ............ *A61K 51/1217* (2013.01); *A61K 9/19* (2013.01); *A61K 47/183* (2013.01); *A61K 47/20* (2013.01); *A61K 47/38* (2013.01); *A61K 47/42* (2013.01); *A61K 51/025* (2013.01)

(58) Field of Classification Search
CPC .... A61K 51/1217; A61K 9/19; A61K 47/183; A61K 47/20; A61K 47/38; A61K 47/42; A61K 51/025
See application file for complete search history.

(56) References Cited

PUBLICATIONS

Richard J. Kowalsky, Technetium Radiopharmaceutical Chemistry, The The University of New Mexico Health Sciences Center, College of Pharmacy, Albuquerque, New Mexico, 2006, vol. 12, Lesson 3, pp. 1-77; Dec. 31, 2006. (Year: 2006).*

Mrinal K. Dewanjee, The Chemistry of 99mTc-Labeled Radiopharmaceuticals, Seminars in Nuclear Medicine, vol. 20, Issue 1, 1990, pp. 5-27; Jan. 1990 (Year: 1990).*

* cited by examiner

*Primary Examiner* — Robert S Cabral
(74) *Attorney, Agent, or Firm* — William D. Hare, Esq.; McNeely, Hare & War, LLP

(57) ABSTRACT

The present invention relates to stable pharmaceutical compositions of sulfur colloid, which advantageously provide a high radiochemical purity to $^{99m}$Tc-pertechnetate without causing the gel formation. The compositions include pre-lyophilized and lyophilized compositions of sulfur colloid. It also relates to a non-radioactive kit which upon reconstitution with $^{99m}$Tc-pertechnetate solution gives stabilized $^{99m}$mTc-Sulfur colloid radiopharmaceutical composition. Further, the process for preparation of said compositions and their use for diagnostic purposes are also disclosed.

20 Claims, No Drawings

PHARMACEUTICAL COMPOSITIONS OF SULFUR COLLOID AND PROCESSES THEREOF

TECHNICAL FIELD

The present invention relates to stable pharmaceutical compositions of sulfur colloid. The compositions include pre-lyophilized and lyophilized compositions of sulfur colloid. It also relates to a non-radioactive kit which upon reconstitution with $^{99m}$Tc-pertechnetate solution gives stabilized $^{99m}$Tc-Sulfur colloid radiopharmaceutical composition. Further, the process for preparation of said compositions and their use for diagnostic purpose are also disclosed.

BACKGROUND

Radiopharmaceuticals based on the technetium-99 m ($^{99m}$Tc) are used in diagnostic nuclear medicine for in-vivo imaging. Sulfur colloid kit is used in reticuloendothelial imaging, gastroesophageal reflux scintigraphy, peritoneovenous (LeVeen) shunt patency.

U.S. Pat. No. 3,683,066, assigned to Ivan discloses the use of chelating agent to prevent flocculation.

The commercially available preparations of sulfur colloid comprises gelatin, which plays pivotal role for stability and protection of colloid. However, it has been observed that use of gelatin increases viscosity of composition prior to lyophilization and adversely impact manufacturing at laboratory scale as well as at commercial scale. The inventors of present invention have found that exposure of pre-lyophilized composition to lower temperature conditions for longer duration leads to increase in viscosity of bulk solution and it further solidifies to thick gel. It becomes literally impossible for semi solid or gel compositions to pass through filter membranes and to fill the pre-lyophilized composition in the vials for lyophilization.

Prior art does not disclose gelling or viscosity problem during manufacturing of stable sulfur colloid compositions. It has been surprisingly found by inventors that appropriate heating time and/or temperature are critical for sulfur colloid compositions which needs to be monitored and controlled during manufacturing to have appropriate viscosity and avoid gelling.

The compositions prepared according to present invention are found to be stable, have high radiochemical purity, appropriate bio-distribution profile. The processes according to present invention are reproducible, simple and suitable for industrial production.

SUMMARY

It is the principal object of the present invention, to provide a stable pharmaceutical compositions of sulfur colloid wherein, the pharmaceutical composition has a viscosity in the range from about 1 cP to about 100 cP at 2° C. to 25° C. for at least 2 hours, preferably for at least 8 hours, preferably for at least 12 hours, preferably for at least 24 hours, most preferably for at least 30 hours.

It is another object of the present invention, to provide a lyophilized non-radioactive kit which upon reconstitution with $^{99m}$Tc-pertechnetate solution provides a stabilized $^{99m}$Tc-sulfur colloid radiopharmaceutical composition with desired technical attribute.

It is another object of the present invention, to provide a process for the preparation of said radiopharmaceutical compositions and their use for diagnostic purposes.

It is another object of the present invention, to provide a pharmaceutical composition of sulfur colloid comprising: a reducing agent; a colloid support agent; a chelating agent and optionally one or more excipients selected from antimicrobial agent or radio protectant, wherein the pharmaceutical composition, has a viscosity in the range from about 1 cP to about 100 cP at 2° C. to 25° C. for at least 2 hours, preferably for at least 8 hours, preferably for at least 12 hours, preferably for at least 24 hours, most preferably for at least 30 hours.

It is another object of the present invention, to provide a pharmaceutical composition of sulfur colloid prepared by a process comprising: preparing a bulk solution by mixing gelatin with water for injection; heating the colloidal supporting agent for at least 100° C. for about 110-150 minutes; adding reducing agent; adding a chelating agent with stirring wherein the composition has a viscosity in the range from about 1 cP to about 100 cP at 2° C. to 25° C. for at least 2 hours, preferably for at least 8 hours, preferably for at least 12 hours, preferably for at least 24 hours, most preferably for at least 30 hours It is another object of the present invention, to provide the compositions prepared according to the process of present invention with desirable technical attributes such as stability, shelf life, high radiochemical purity (RCP) and bio-distribution.

DETAILED DESCRIPTION

Sulfur colloid kit comprises a lyophilized vial comprising sodium thiosulfate, edetate disodium and bovine gelatin. The kit further comprises two solutions hydrochloric acid, sodium bisphosphonate and sodium hydroxide. The final composition is prepared by adding $^{99m}$Tc pertechnetate solution into lyophilized vial and subsequently adding two solutions into lyophilized vial. During process, elemental sulfur precipitates out of the solution to form colloidal size particles containing $^{99m}$Tc$_2$S$_7$.

Gelatin plays pivotal role for stability and protection of colloid. However, use of gelatin tends to increase the viscosity of pre-lyophilized composition at lower temperature conditions which impact manufacturability at laboratory scale as well as at commercial scale.

As used herein, the term "sulfur colloid" encompasses radiopharmaceutical compositions.

As used herein, the term 'kit' comprises lyophilized composition vial, acid solution and buffer solution.

As used herein, the term "radioisotope" or "radionuclide" are radioactive isotopes of an element. They can also be defined as atoms that contain an unstable combination of neutrons and protons, or excess energy in their nucleus.

As used herein, the term "composition", as in pharmaceutical composition, is intended to encompass a diagnostic product comprising reducing agent and other inert ingredients (pharmaceutically acceptable excipients). Such pharmaceutical compositions are synonymous with "formulation" and "dosage form".

As used herein, the term "pharmaceutical composition", refers to pre-lyophilized composition or bulk composition, lyophilized composition.

As used herein, the term "pre-lyophilized composition or bulk composition" comprises reducing agent, colloid support agent, chelating agent and one or more pharmaceutically acceptable excipients prior to lyophilization in a solution form.

As used herein, the term "lyophilized composition" is intended to encompass a freeze-dried composition of sulfur colloid and one or more pharmaceutically acceptable excipients.

As used herein, the term "radiopharmaceutical composition" is intended to encompass lyophilized sulfur colloid composition, an acidifier, a buffer solution reconstituted with radioisotope $^{99m}$Tc.

As used herein, the term "gel or gelling" refers to solid or semi-solid consistency having a viscosity ranging from 10-1000 centipoise.

As used herein, the term "excipient" means an inactive component in the kit such as a biocompatible reductant, chelating agent, pH adjusting agent, filler, radio protectant, colloid support agent, antimicrobial preservatives and the like. The excipients that are useful in preparing a pharmaceutical composition are generally safe, non-toxic and are acceptable for human pharmaceutical use. Reference to an excipient includes both one and more than one such excipient. Combination of excipients performing the same function may also be used to achieve desired composition characteristics.

As used herein, the term "reducing agent" means a compound, which is capable of donating sulfur. Suitable reducing agents as per the present invention include, but are not limited to sodium dithionite, stannous sulfide, sodium bisulphite, formamidine sulphonic acid, and sodium thiosulfate or combinations thereof. The preferred reducing agent comprises sodium thiosulfate or stannous sulfide. The amount of reducing agent in the radiopharmaceutical composition is from about 1% to about 15%. Preferably from about 5% to about 12%, most preferably from about 7% to about 11% based on total weight of the composition As used herein, the term "colloid support agent" means a compound, which is capable of stabilizing colloid. Suitable colloid support agents as per the present invention include, but are not limited to gelatin, alginic acid, guar gum, bentonite, carbomer, carrageenan, colloidal silicon dioxide, cellulose derivatives, tragacanth, poloxamer, carboxymethylcellulose or combination thereof. The preferred colloid support agent according to the present invention comprises gelatin, cellulose derivatives. The amount of colloid support agent in the radiopharmaceutical composition is from about 50% to about 95% preferably from about 60% to about 95%, most preferably from about 70% to about 85% based on total weight of the composition.

As used herein, the term "chelating agent" also referred to as transfer ligand or intermediate ligand, a compound that prevents flocculation and provide stability. Suitable chelating agents according to the present invention include but not limited to disodium edetate,((1,2-cyclohexylene)oxyethylene)dinitrilo)tetraaceticacid; (oxybis (ethylenenitrilo))tetraacetic acid; (1,2-cyclohexylenedinitrilo)tetraacetic acid; N-(5-(3-(5-aminopentyl)-hydroxycarbamoyl) propionamido) pentyl)-3-((5-(N-hydroxyacetamido)-pentyl) carbamoyl) propionohydroxamic acid; diethyldithiocarbamic acid sodium salt; (diethylenetrinitrilo) pentaacetic acid; (diethylenetrinitrilo) pentaacetic acid pentaethyl ester; (ethylenedinitrilo)-tetraacetic acid; ((2-(3-oxomorpholino)ethyl)imino) diacetic acid, diethyl ester; and ((2-mercaptoethyl)imino) diacetic acid, cyclohexanediamine tetraacetic acid (CDTA), hydroxyethylethylenediamine triacetic acid (HEDTA), diethylenetriamine pentaacetic acid (DTPA), dimercaptopropane sulfonic acid (DMPS), dimercaptosuccinic acid (DMSA), aminotrimethylene phosphonic acid (ATPA), citric acid or combinations thereof. The preferred reducing agent comprises disodium edetate or diethylenetriamine pentaacetic acid (DTPA). The amount of chelating agent in the radiopharmaceutical composition is from about 5% to about 20% preferably from about 7% to about 15%, most preferably from about 8% to about 13% based on total weight of the composition.

As used herein, the term "pH-adjusting agents" refers to a compound or mixture of compounds capable of maintaining the pH of the radiopharmaceutical composition within limits acceptable for human administration. Suitable pH adjusting agents according to the present invention include but not limited to sodium hydroxide, hydrochloric acid, acetic acid, fumaric acid or combinations thereof.

As used herein, the term "radioprotectant" means a compound, which prevents degradation reactions, such as redox reactions, by trapping highly reactive free radical species such as oxygen containing free radicals generated from the radiolysis of water. Radioprotectants of the present invention include, but are not limited to para-aminobenzoic acid, gentisic acid, citric acid, acetic acid, fumaric acid, tartaric acid, maleic acid, anthranilic acid or their pharmaceutically acceptable salts thereof and combinations thereof. The preferred radioprotectant comprises gentisic acid, ascorbic acid, para-aminobenzoic acid, maleic acid. The concentration of radioprotectant in the radiopharmaceutical composition is from about 0.01% to about 5%.

As used herein, the term "antimicrobial preservative" means an agent capable of preventing the growth of potentially harmful microorganisms such as bacteria, yeasts or moulds. Suitable antimicrobial preservatives according to the present invention include, but are not limited to benzalkonium chloride, benzethonium chloride, benzyl alcohol, cresol, cetrimide, thiomersal phenol, paraben. The preferred antimicrobial preservative comprises benzalkonium chloride, benzethonium chloride, paraben, benzyl alcohol.

As used herein "Viscosity" refers to the resistance of a liquid to flow. The units of viscosity are $Ns/m^2$, known as Pascal-seconds (Pa-s).

As used herein "absolute Viscosity" refers to the force needed by a fluid to overcome its own internal molecular friction so that it can flow. The units of viscosity are $Ns/m^2$, known as Pascal-seconds (Pa-s), Poise (P), Centipoise (cP).

As used herein "Controlled room temperature" refers to temperature maintained thermostatically that encompasses working environment of 20°-25° (68°–77° F.).

As used herein, the term "about" means±approximately 20% of the indicated value, such that "about 10 percent" indicates approximately 8 to 12 percent.

In one aspect of the present invention, provided herein are the stabilized pharmaceutical compositions of sulfur colloid.

In another aspect of the present invention, provided herein are the stabilized pharmaceutical compositions of sulfur colloid comprising reducing agent, colloid support agent, chelating agent and one or more additional excipient.

In yet another aspect of the present invention, provided herein are the stabilized pharmaceutical compositions of sulfur colloid, wherein composition may optionally contain radioprotectant or antimicrobial preservatives.

In another aspect, the present invention includes a stable non-radioactive composition comprising reducing agent, wherein the pH of the composition after reconstitution with water or saline is from about 4.0 to about 9.0, and preferably from about 4.5 to about 7.5.

In yet another aspect of the present invention, the pharmaceutical composition of sulfur colloid comprises a reducing agent; a colloid support agent; a chelating agent and optionally one or more excipients selected from antimicrobial agent or radioprotectant; wherein the pharmaceutical composition has a viscosity in the range from about 1 cP to about 100 cP at 2° C. to 25° C. for at least 2 hours, preferably for at least 8 hours, preferably for at least 12 hours, preferably for at least 24 hours, most preferably for at least 30 hours.

In yet another aspect of the present invention, the pharmaceutical composition of sulfur colloid is provided, wherein the pharmaceutical composition, has a viscosity in the range of about 1 cP to about 50 cP, preferably about 1 cP to about 30 cP, preferably about 1 cP to 20 cP, preferably about 1 cP to 10 cP, preferably about 1 cP to 5 cP and most preferably below 3 cP at about 5° C. to 25° C. for at least 2 hours, preferably for at least 8 hours, preferably for at least 12 hours, preferably for at least 24 hours, most preferably for at least 30 hours.

In yet another aspect of the present invention, the pharmaceutical composition of sulfur colloid is provided, wherein the pharmaceutical composition has a viscosity in the range of about 1 cP to about 50 cP, preferably about 1 cP to about 30 cP, preferably about 1 cP to 20 cP, preferably about 1 cP to 10 cP, preferably about 1 cP to 5 cP and most preferably below 3 cP at about 5° C. to 25° C. for at least 2 hours, preferably for at least 8 hours, preferably for at least 12 hours, preferably for at least 24 hours, preferably for at least 30 hours most preferably not less than 36 hours In yet another aspect of the present invention, the pharmaceutical composition of sulfur colloid is provided, wherein the composition does not form a gel within a period of at least 2 hours, preferably for at least 8 hours, preferably for at least 12 hours, preferably for at least 24 hours and most preferably up to 36 hours at 5° C. to 25° C.

In yet another aspect of the present invention, the pharmaceutical composition of sulfur colloid is prepared by a process comprising: preparing a bulk solution by mixing gelatin with water for injection; heating the colloidal supporting agent solution at least 100° C. for 60 minutes or more; adding a reducing agent; adding a chelating agent; wherein the composition has a viscosity in the range from about 1 cP to about 100 cP at 5° C. to 25° C. Preferably, the heating step lasts for between about 60 minutes to about 180 minutes; between about 80 minutes to about 170 minutes; between about 90 minutes to about 160 minutes; between about 100 minutes to about 150 minutes; or between about 110 minutes to about 150 minutes.

In yet another aspect of the present invention, the pharmaceutical composition of sulfur colloid does not form a gel within a period of at least 2 hours at a temperature of 20±5° C., preferably at 10° C. to 20° C.

In yet another aspect of the present invention, the process of preparing the lyophilized composition is provided. Lyophilization is the process which comprises three steps a) freezing (solidification) b) primary drying (ice sublimation) c) secondary drying (moisture desorption). Vials containing a pre lyophilized composition are loaded on temperature controlled trays within a sterile chamber which are cooled to low temperatures until completely solidified. After freezing, chamber pressure is reduced and shelf temperature is raised to remove the frozen solvent via sublimation. The remaining unfrozen solvent that is chemically bound to the solid product is then removed by a desorption process. The vials are stoppered in the chamber under inert gas environment and/or vacuum concluding the drying process. The final product is called a cake and occupies approximately the same volume as the initial liquid fill because of its high porosity. In order to ensure high quality products are consistently produced, it is important to be able to control and provide repeatability of the lyophilization cycles.

In one aspect of the present invention, provided herein are the stabilized radiopharmaceutical compositions of sulfur colloid.

In another aspect of the present invention, provided herein are the stabilized radiopharmaceutical compositions of sulfur colloid comprising reducing agent, colloid support agent, chelating agent and one or more additional excipient.

In yet another aspect of the present invention, provided herein are the stabilized radiopharmaceutical compositions of sulfur colloid, wherein composition may optionally contain radioprotectant or antimicrobial preservatives.

In yet another aspect of the present invention, provided herein are the lyophilized, non-radioactive kit which upon reconstitution with $^{99m}$Tc-pertechnetate solution gives a stabilized $^{99m}$Tc-sulfur colloid radiopharmaceutical composition includes first vial comprising reducing agent, colloid support agent, chelating agent and pharmaceutically acceptable excipients thereof; second vial comprising $^{99m}$Tc-pertechnetate, third vial comprising buffer; fourth vial comprising pH adjusters.

In yet another aspect of the present invention, the lyophilized composition when stored for six months at 40° C.±2° C., relative humidity 75%±5% and reconstituted with a $^{99m}$Tc-pertechnetate solution, the composition has a radiochemical purity of at least 95% for at least 6 hours at temperature of 15° C. to 25° C. following said reconstitution.

In yet another aspect of the present invention, the lyophilized composition when stored for six months at 40° C.±2° C. relative humidity 75%±5% and reconstituted with a $^{99m}$Tc-pertechnetate solution, the composition has a radiochemical purity of at least 95% for at least 12 hours at temperature of 15° C. to 25° C. following said reconstitution.

In yet another aspect of the present invention, the lyophilized composition when stored for six months at 40° C.±2° C. relative humidity 75%±5% and reconstituted with a $^{99m}$Tc-pertechnetate solution, the composition has a radiochemical purity of at least 95% for at least 24 hours at temperature of 15° C. to 25° C. following said reconstitution.

In yet another aspect of the present invention, the lyophilized composition when stored for six months at 40° C.±2° C. relative humidity 75%±5% and reconstituted with a $^{99m}$Tc-pertechnetate solution, the composition has a radiochemical purity of at least 99% for at least 6 hours at temperature of 15° C. to 25° C. following said reconstitution.

In yet another aspect of the present invention, the lyophilized composition when stored for six months at 40° C.±2° C. relative humidity 75%±5% and reconstituted with a $^{99m}$Tc-pertechnetate solution, the composition has a radiochemical purity of at least 99% for at least 12 hours at temperature of 15° C. to 25° C. following said reconstitution.

In yet another aspect of the present invention, the lyophilized composition when stored for six months at 40° C.±2° C. relative humidity 75%±5% and reconstituted with a $^{99m}$Tc-pertechnetate solution, the composition has a radiochemical purity of at least 99% for at least 24 hours at temperature of 15° C. to 25° C. following said reconstitution.

According to another aspect of the present invention, the kit is a unit dose or multi dose kit.

In yet another aspect of the present invention, provided herein is a suitable clinical grade container or vial or pre-filled syringes suitable for administration in humans.

The final composition of the present invention is packed in a 10 mL Type I glass vial. In one embodiment of the present invention, the composition can be filled into a container such as a vial, an ampoule, or a prefilled syringe of 0.5 ml, 1 ml, 2 ml, 3 ml, 5 ml, 10 ml, 20 ml, 25 ml, 30 ml, 60 ml or 100 ml.

In yet another aspect of the present invention includes a stable radioactive $^{99m}$Tc sulfur colloid composition, wherein the particle size of composition is about 0.1 μ-2.0 μ in diameter.

The 'inert gas' according to the present invention can be selected from group consisting of helium, neon, argon, nitrogen or combinations thereof. In an embodiment of the invention, an inert gas is used to replace the presence of air in a vial containing the composition of the present invention during transportation and storage, and until the vial is opened.

In yet another aspect of the present invention, the pre-lyophilized liquid compositions of the present invention comprises less than 5 ppm of oxygen content, preferably less than 2 ppm, and most preferably less than 1 ppm.

In yet another aspect of the present invention, the lyophilized composition of the present invention comprises less than 5 percent of oxygen content in the head space of the vial, preferably less than 2 percent, less than 1 percent, less than 0.5 percent.

The oxygen content in the composition is maintained using an inert gas selected from the group consisting of helium, nitrogen, carbon dioxide, argon, vacuum, or combination thereof.

In yet another aspect of the present invention, provided herein is the use of a stabilized radiopharmaceutical composition of sulfur colloid and one or more pharmaceutically acceptable excipients in the imaging areas of functioning reticuloendothelial cells in the liver, spleen and bone marrow, and related diagnostic methods.

EXAMPLES

The following examples are intended to further illustrate certain preferred embodiments of the invention and are not limiting in nature. The composition according to the present invention per vial comprises:

TABLE 1

PHARMACEUTICAL COMPOSITIONS

| Ingredients | Amount (% w/w) | | | |
|---|---|---|---|---|
| | Example 1 | Example 2 | Example 3 | Example 4 |
| Sodium thiosulfate | 5 | 9 | 8.9 | 8.9 |
| Gelatin | 82.5 | 81 | 80.8 | 80.8 |
| Edetate disodium | 12.5 | 10 | 10.2 | 10.2 |
| Radioprotectant | — | — | — | 0.01-5 |
| Water for Injection | q.s | q.s | q.s | q.s |

Experiments: Pharmaceutical composition of sulfur colloid is prepared by mixing gelatin with water for injection to get a clear solution. The solution is heated from about 80° C. to 130° C. The composition was prepared by adding reducing agent and chelating agent to the gelatin solution. The final compositions according to Examples 1, 2 and 3 were stored at a temperature of 25±5° C. for 24 hours.

Gelling behavior at different temperature conditions were studied using compositions according to Examples 1, 2 and 3.

TABLE 2

GELLING BEHAVIOUR AT CONTROLLED ROOM TEMPERATURE

| S. No | Heating Temperature (° C.) | Heating Time (min) | Observations at CRT | |
|---|---|---|---|---|
| | | | 8 hrs | 24 hrs |
| 1 | 40° C.-100° C. | 15 | Gelling | Gelling |
| 2 | 118° C.-150° C. | 15 | No gelling | No gelling |

From above results, it was observed that heating for at least 100° C. was found to be essential for preventing gelling of pre-lyophilized composition for at least 24 hours.

The operating temperature for bulk manufacturing of sulfur colloid compositions according to the present invention ranges from 10-18° C. Therefore, gelling behavior of compositions as per Example 1, 2, 3 was studied at operating temperature.

TABLE 3

GELLING BEHAVIOUR AT OPERATING TEMPERATURE CONDITIONS (10-18° C.)

| S. No. | Heating Temperature (° C.) | Heating Time (min) | Gelling Observations (10-18° C.) |
|---|---|---|---|
| 1 | 121° C. | 15 | Gelling within 20 minutes |
| 2 | 121° C. | 60 | Gelling within 120 minutes |
| 3 | 115° C. | 110 | Gelling within 22 hours |
| 4 | 130° C. | 60 | Gelling within 22 hours |
| 5 | 118-125° C. | 100-120 | No gelling for 30 hours |
| 6 | 121° C. | 150 | No gelling for 30 hours |

Above results indicate that both the temperature and duration of heating plays an important role in the gelling behaviour of the compositions. The gelatin solution needs to be heated to at least 100° C. for 100-150 min. These operating conditions prevented the gelling of sulfur colloid compositions for 30 hours. This provided abundant flexibility in executing filtration and filling of final bulk solution into vials for lyophilization.

The compositions according to Examples 1 and 2 were prepared by heating gelatin solution for not less than 100 minutes at a minimum temperature of 100° C. were lyophilized and gelling behaviour of the reconstituted product with water for injection were checked.

TABLE 4

GELLING BEHAVIOUR OF RECONSTITUED COMPOSITION

| S. No | Heating Temperature (° C.) | Heating Time (min) | Observations At below 15° C. |
|---|---|---|---|
| 1 | Not less than 100° C. | Not less than 100 | No gelling up to 36 hrs |

From above experiments, it was observed that appropriate viscosity of the compositions according to present invention is important for manufacturing. The compositions should not gel or become semi solid at operational conditions. The composition should have a viscosity between 1-100 cp 20±5° C., preferably below 50 cp at 20±5° C., preferably below 10 cp at 20±5° C., preferably below 5 cp at 20±5° C., preferably below 3 cp at 20±5° C., preferably below 2 cp at 20±5° C., preferably below 1 cp at 20±5° C.

TABLE 5

VISCOSITY OF COMPOSITIONS
The viscosity was measured using modular compact rheometer,
Model: MCR 102 by Anton Paar using cone plate method at different
process conditions at a temperature from 5° C. to 25° C.

| S. No | Process condition | Viscosity (cP) | | | | |
|---|---|---|---|---|---|---|
| | | 5° C. | 10° C. | 15° C. | 20° C. | 25° C. |
| 1 | 121° C./15 min | 127.3 | 103 | 48.7 | 11.7 | 5.3 |
| 2 | 121° C./60 min | 3.5 | 3.1 | 2.5 | 2 | 1.7 |
| 3 | 121° C./120 min | 2.7 | 2.3 | 1.9 | 1.6 | 1.4 |
| 4 | 121° C./150 min | 2.2 | 1.9 | 1.6 | 1.3 | 1.2 |

The compositions according to Examples 1, 2 and 3 prepared according the present invention were checked for radiochemical purity and bio distribution and found to be acceptable.

Radiochemical purity of the reconstituted test formulations prepared according to present invention was measured using USP method. The test formulation was stored at accelerated stability condition (Temperature: 40° C.±2° C.; Relative Humidity: 75%±5%) up to six months and exhibited RCP of at least 99 percent when reconstituted with sodium pertechnetate and stored at a temperature of 15° C. to 25° C. for at least 6 hours. Storage for six months at higher temperature than ambient temperature is equivalent for longer storage time at ambient temperature. Therefore, the storage has been tested for six months at a temperature of 40° C.±2° C. and a relative humidity of 75%±5%, which is known to be equivalent to 2 years storage at 20-25° C. (ambient temperature).

TABLE 6

RADIOCHEMICAL PURITY AND BIODISTRIBUTION

| Parameter | | Initial | 3 Months | 6 Months |
|---|---|---|---|---|
| RCP | Initial | 99.7 | 99.7 | 99.0 |
| ($^{99m}$Tc-Sulfur Colloid | 6 hours | 99.8 | 99.9 | 99.0 |
| Complex) | 24 hours | 100 | 100 | 100 |
| Bio-distribution | Initial | Complies | Complies | Complies |
| | 6 Hours | Complies | Complies | Complies |
| | 24 hours | Complies | Complies | Complies |

While this invention has been described in detail with reference to certain preferred embodiments, it should be appreciated that the present invention is not limited to those precise embodiments. Rather, in view of the present disclosure, which describes the current best mode for practicing the invention, many modifications and variations would present themselves to those skilled in the art without departing from the scope, and spirit of this invention.

We claim:

1. A pharmaceutical composition of sulfur colloid comprising:
   a. a reducing agent, the reducing agent comprising sodium thiosulfate at from 5% to 12% based on total weight of the composition without water;
   b. gelatin at from 70% to 85% based on total weight of the composition without water;
   c. a chelating agent, the chelating agent comprising edetate disodium at from 5% to 20% based on total weight of the composition without water; and
   d. water,
   made by a process that includes the steps of preparing a gelatin solution by mixing gelatin with water and heating the gelatin solution at a temperature of at least 100° C. for a period of 100 minutes or more;
   wherein the pharmaceutical composition does not form a gel when stored at 5° C. to 25° C. for up to 36 hours after manufacture as determined by having a viscosity of about 1 cP to about 100 cP at a temperature of 2° C. to 25° C.

2. The pharmaceutical composition according to claim 1, further comprising one or more excipients selected from the group consisting of antimicrobial agent or radioprotectant.

3. The pharmaceutical composition according to claim 1, wherein the viscosity is less than 10 cP for a duration of up to 30 hours.

4. The pharmaceutical composition according to claim 1, wherein the viscosity is less than 5 cP for a duration of up to 30 hours.

5. The pharmaceutical composition according to claim 1, wherein the viscosity is less than 3 cP for a duration of up to 30 hours.

6. The pharmaceutical composition according to claim 1, further comprising a step of lyophilizing, wherein, when said composition is lyophilized, stored for six months and reconstituted with a $^{99m}$Tc-pertechnetate solution, the composition has a radiochemical purity of at least 99% for at least 6 hours at temperature of 15° C. to 25° C. following said reconstitution.

7. A method for performing reticuloendothelial imaging, gastroesophageal reflux scintigraphy or peritoneo-venous shunt patency in a patient, the method comprising administering a radiopharmaceutical composition to the patient, wherein the radiopharmaceutical comprises the pharmaceutical composition of claim 1 combined with a $^{99m}$Tc pertechnetate solution.

8. A radiopharmaceutical composition comprising a pharmaceutical composition according to of claim 1 combined with a $^{99m}$Tc pertechnetate solution.

9. The pharmaceutical composition of claim 1, wherein the process further comprises the steps of:
   adding the sodium thiosulfate and the edetate disodium into the solution.

10. The pharmaceutical composition of claim 1, wherein the heating is for a period of about 110 minutes to about 150 minutes.

11. A process for the preparation of a lyophilized composition comprising the steps of:
   a. preparing a gelatin solution by mixing gelatin with water;
   b. heating the gelatin solution of step (a) to a temperature of between 100° C. to 150° C. for at least 100 minutes;
   c. adding a reducing agent comprising sodium thiosulfate to the solution of step (b);
   d. adding a chelating agent comprising edetate disodium to the solution of step (c); and
   e. lyophilizing the solution of step (d)
   wherein the composition resulting from step (d) does not form a gel when stored at 5° C. to 25° C. for up to 36 hours after forming step (d) as determined by having a viscosity of from about 1 cP to about 100 cP at a temperature of 2° C. to 25° C.

12. The process of claim 11, wherein the sodium thiosulfate comprises about 5% to about 12% by weight of the composition without water.

13. The process of claim 11, wherein the gelatin comprises about 70% to about 85% by weight of the composition without water.

14. The process of claim 11, wherein the edetate disodium comprises about 5% to about 20% by weight of the composition without water.

15. The process of claim 11, wherein the sodium thiosulfate comprises about 5% to about 12% by weight of the composition without water, the gelatin comprises about 70% to about 85% by weight of the composition without water, and the edetate disodium comprises about 5% to about 20% by weight of the composition without water.

16. The process of claim 11, further comprising reconstituting the lyophilized composition of step (e) with a $^{99m}$Tc pertechnetate solution.

17. The process of claim 15, further comprising reconstituting the lyophilized composition of step (e) with a $^{99m}$Tc pertechnetate solution.

18. A radiopharmaceutical composition comprising the composition according to claim 11 reconstituted with a $^{99m}$Tc pertechnetate solution.

19. A process for the preparation of a lyophilized composition, the process consisting of:
   a. preparing a gelatin solution by mixing gelatin with water;
   b. heating the gelatin solution of step (a) to a temperature of between 100° C. to 150° C. for between 100 minutes and 150 minutes;
   c. adding a reducing agent comprising sodium thiosulfate to the solution of step (b);
   d. adding a chelating agent comprising edetate disodium to the solution of step (c); and
   e. lyophilizing the solution of step (d);
   wherein the composition resulting from step (d) does not form a gel when stored at 5° C. to 25° C. for up to 36 hours after forming step (d) as determined by having a viscosity of about 1 cP to about 100 cP at a temperature of 2° C. to 25° C.

20. The process of claim 19, wherein the sodium thiosulfate comprises about 5% to about 12% by weight of the composition without water, the gelatin comprises about 70% to about 85% by weight of the composition without water, and the edetate disodium comprises about 5% to about 20% by weight of the composition without water.

* * * * *